United States Patent [19]
Ishikawa et al.

[11] Patent Number: 6,133,012
[45] Date of Patent: Oct. 17, 2000

[54] THERMOSTABLE ACYL PEPTIDE HYDROLASE AND GENE ENCODING THE SAME

[75] Inventors: Kazuhiko Ishikawa; Ikuo Matsui; Hiroyasu Ishida; Yoshitsugu Kosugi; Katsuhiko Higuchi, all of Ibaraki, Japan

[73] Assignee: Director General of Agency of Industrial Science & Technology, Tokyo, Japan

[21] Appl. No.: 09/016,080

[22] Filed: Jan. 30, 1998

[30] Foreign Application Priority Data

Jan. 31, 1997 [JP] Japan ................................ 9-018381

[51] Int. Cl.[7] .................................................. C12N 9/52
[52] U.S. Cl. .............................................. 435/220
[58] Field of Search ...................................... 435/212, 219, 435/220

[56] References Cited

PUBLICATIONS

Ishikawa, K., et al. (1997) Pro. Eng. 10 (suppl), 63.
Mori, N., et al. (1990) Agric. Biol. Chem. 54(1), 263–265.
Ishikawa, K, et al. (1998) J. Biol. Chem. 273(28), 17726–17731.

*Primary Examiner*—Charles L. Patterson, Jr.
*Attorney, Agent, or Firm*—Fish & Richardson P.C.

[57] ABSTRACT

An acyl peptide hydrolase having an optimum temperature range of 90–95° C. and a gene encoding the same are disclosed. With the above enzyme, it becomes possible to conduct amino terminal analysis of acylated proteins and peptides at high temperatures.

3 Claims, 1 Drawing Sheet

THERMOSTABLE ACYL PEPTIDE HYDROLASE AND GENE ENCODING THE SAME

BACKGROUND OF THE INVENTION

1. Field of the Invention

The present invention relates to a thermostable acyl peptide hydrolase and a gene encoding the same. The enzyme of the present invention catalyzes a reaction to liberate an acyl amino acid alone from a protein or peptide having an acylated amino terminal, and thus is effective in amino terminal analysis.

2. Prior Art

Conventionally, mammal-derived acyl peptide hydrolases have been used for the analysis of acylated amino terminals of proteins and peptides.

Since such conventional enzymes are unstable at high temperatures, it has been necessary to perform the reaction described above at relatively low temperatures. However, performing the above reaction at a high temperature could bring a number of advantages, such as improvement of reaction efficiency, removal of microorganisms mixed in, etc. An enzyme which can be used at high temperatures and which is stable under high temperatures is strongly demanded. The present invention has been made under such technical circumstances, and it was an object of the invention to provide a thermostable acyl peptide hydrolase.

Toward the solution of the above problem, the inventor of the present invention paid attention to a superthermophilic bacterium thriving at 90–100° C. and has found in its gene sequences a gene that is presumed to exhibit a thermostable acyl peptide hydrolase activity. Further, the inventor has produced an enzyme from the above gene using *Escherichia coli* and confirmed that the resultant enzyme is stable at high temperatures (90–95° C.) and yet exhibits an acyl peptide hydrolase activity under such temperatures. Based on these findings, the present invention has been achieved.

SUMMARY OF THE INVENTION

The present invention relates to an enzyme having the following properties:
(1) it hydrolyzes acyl peptides;
(2) it has an optimum temperature range of 90–95° C.;
(3) it has an optimum pH range of 5.0–6.0;
(4) it does not loose its activity even when heated at 95° C. for 3 hours at pH 7.5; and
(5) it has a molecular weight of about 60,000 as determined by SDS polyacrylamide gel electrophoresis.

The present invention also relates to a gene coding for the following protein (a) or (b):
(a) a protein having the amino acid sequence shown in SEQ ID NO: 1
(b) a protein which has the amino acid sequence shown in SEQ ID NO: 1 having deletion, substitution or addition of one or several amino acids and which has an ability to hydrolyze acyl peptides.

DETAILED DESCRIPTION OF THE INVENTION

Figure 1:
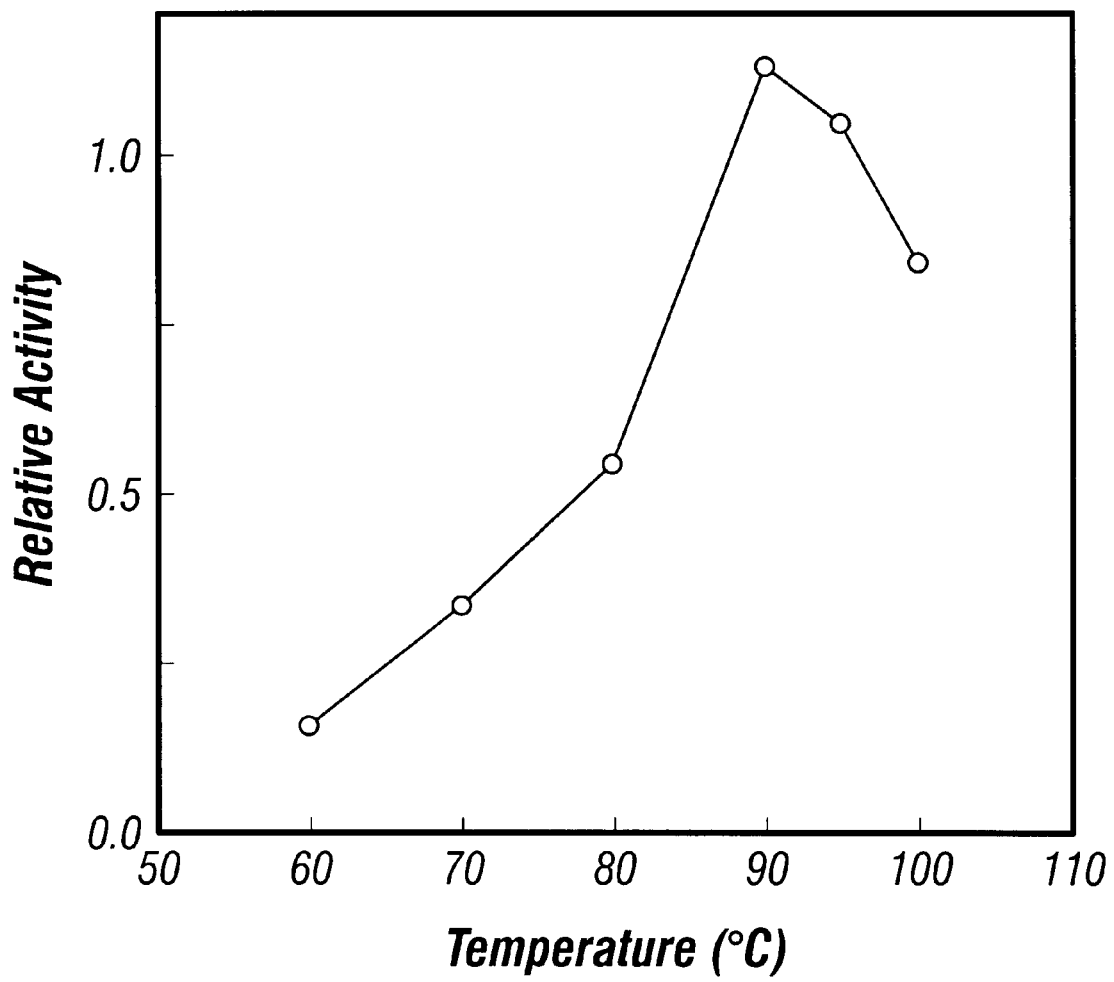
FIG. 1 is a graph showing changes in enzyme activity caused by temperature changes.

Hereinbelow, the present invention will be described in detail.

The enzyme of the invention has the following properties:
(1) The substrate of this enzyme is acyl peptides and it hydrolyzes them.
(2) Changes in its enzyme activity caused by temperature changes are as shown in FIG. 1. As seen from this Figure, the optimum temperature range of this enzyme is 90–95° C., the most preferable temperature being 90° C.
(3) The optimum pH range is 5.0–5.5, the most preferable pH being 5.5.
(4) This enzyme is thermostable, and it does not loose its enzyme activity even when heated at 95° C. for 3 hours (at pH 7.5).
(5) The molecular weight of this enzyme is about 60,000 as determined by SDS polyacrylamide gel electrophoresis, and its length is 400 nm.

The amino acid sequence for the enzyme of the invention can be represented by the amino acid sequence shown in SEQ ID NO: 1 or the amino acid sequence shown in SEQ ID NO: 1 having deletion, substitution or addition of one or several amino acids. The term "one or several amino acids" used herein means a number of amino acids which can be deleted, substituted or added by the site specific mutagenesis (Nucleic Acid Research, Vol. 10, No. 20, pp. 6487–6500).

Since the enzyme of the invention is contained in microorganism cells, it can be obtained from them. Specifically, cells of a microorganism containing the enzyme are crushed and then suspended in a buffer. The resultant cell suspension is centrifuged to obtain a supernatant. Then, the supernatant is purified by various chromatographies with the enzyme activity as an indicator to obtain the enzyme. As the microorganism to be used in the invention, a sulfur-metabolizable archaebacterium *Pyrococcus horikoshi* (The Institute of Physical & Chemical Research, Japan Collection of Microorganisms(JCM) No. 9974; hereinafter referred to as "JCM 9974") may be used, for example. The microorganism to be used is not particularly limited. Any microorganism may be used as long as it can produce the enzyme of the invention. For example, a microorganism incorporating the gene of the invention described later may be used. As the buffer, the conditions of centrifugation and the chromatographies to be used, conventional ones used in purifying an enzyme from a microorganism may be used. The presence or absence of the enzyme activity can be judged by detecting the absorption of p-nitroaniline which is generated by hydrolysis of acyl-amino acid-p-nitroanilide as a substrate.

Since the enzyme of the invention catalyzes a reaction to liberate an acyl amino acid alone from a protein or peptide having an acylated amino terminal, the enzyme is effective in amino terminal analysis.

The gene of the invention codes for a protein having the amino acid sequence shown in SEQ ID NO: 1, or a protein which has the amino acid sequence shown in SEQ ID NO: 1 having deletion, substitution or addition of one or several amino acids and which has aminoacylase activity and carboxypeptidase activity. The term "one or several amino acids" used herein means a number of amino acids which can be deleted, substituted or added by the site specific mutagenesis as described above.

The gene of the invention can be obtained, for example, by the following procedures. First, DNA is extracted from a microorganism having the gene of the invention. The DNA is partially digested with a restriction enzyme, and the resultant DNA fragments are inserted into a vector. This recombinant vector is introduced into an appropriate host microorganism to sequence the DNA fragment. From the resultant sequence data, the homology region of the present enzyme is examined to find out the structural gene thereof.

Then, two primers are synthesized which bind to both ends of the structural gene of the enzyme, respectively. Using these primers, PCR is conducted to amplify the gene of the enzyme alone. Thus, the gene of the enzyme can be obtained. The microorganism having the gene which can be used for this purpose includes, but is not limited to, JCM 9974. The extraction of DNA does not require a special method; it be performed by conventional methods. Commercial kits may be used, if desired. The restriction enzyme to be used is not particularly limited. Preferably, HindIII, EcoRI, XhoI or the like is used. The vector which can be used for this purpose includes, but is not limited to, pBAC108L, pFOS1, pUC19 and M13. The host microorganism which can be used for this purpose includes, but is not limited to, E. coli and yeast. Means to introduce the gene into the host microorganism may be determined depending on the vector to be used. For example, when pBAC108L is used, electroporation is preferable. When pFOS1 is used, it is preferable to use λ phage or the like. An *E. coli* BL21 (DE3) comprising the gene of the invention has been deposited with the National Institute of Bioscience and Human-technology, Agency of Industrial Science and Technology under Accession No. FERM BP-6236 (date of deposit: Jan. 27, 1997), under the terms of Budapest Treaty.

Since the gene of the invention codes for the enzyme of the invention, it is possible to produce the enzyme in large quantity by introducing the gene into a microorganism and expressing it therein. As a vector for gene expression, pET-11a, pET-15a, pET-15b or the like may be used. As a microorganism into which the gene is introduced, *E. coli* BL21 (DE3), *E. coli* XL1-Blue MR or the like may be used.

PREFERRED EMBODIMENTS OF THE INVENTION

Hereinbelow, the present invention will be described in more detail with reference to the following Examples. However, the technical scope of the present invention is not limited by these Examples.

EXAMPLE 1

Cultivation of a Microorganism

JCM 9974 was cultured by the following procedures.

In 1 liter of water, 13.5 g of NaCl, 4 g of $Na_2SO_4$, 0.7 g of KCl, 0.2 g of $NaHCO_3$, 0.1 g of KBr, 30 mg of $H_3BO_3$, 10 g of $MgCl_2 \cdot 6H_2O$, 1.5 g of $CaCl_2$, 25 mg of $SrCl_2$, 1.0 ml of lesazurin solution (0.2 g/L), 1.0 g of yeast extract and 5 g of Bacto-Peptone were dissolved. The pH of the resultant solution was adjusted to 6.8, and the solution was pressure sterilized. Thereafter, hot-air sterilized element sulfur was added thereto to give a concentration of 0.2%. The resultant solution was saturated with argon to obtain an anaerobic medium. Then, JCM 9974 was inoculated thereinto. Whether the medium became anaerobic or not was confirmed by adding $Na_2S$ solution to the medium and observing that the pink color of the lesazurin solution was not formed by the $Na_2S$ in the medium. This culture solution was incubated at 95° C. for 2–4 days and then centrifuged to harvest cells.

EXAMPLE 2

Preparation of Chromosomal DNA

Chromosomal DNA from JCM 9974 was prepared by the following procedures. Briefly, after completion of the cultivation, cells were harvested by centrifuging the culture solution at 5000 rpm for 10 minutes. The cells were washed twice with a buffer containing 10 mM Tris (pH 7.5) and 1 mM EDTA, and then enclosed in an In Cert Agarose (FMC) block. This block was treated in a solution containing 1% N-lauroylsarcosine and 1 mg/ml protease K to thereby separate and prepared the chromosomal DNA in the agarose block.

EXAMPLE 3

Preparation of Library Clones Comprising the Chromosomal DNA

The chromosomal DNA obtained in Example 2 was partially digested with the restriction enzyme Hind III and subjected to agarose gel electrophoresis to thereby prepare DNA fragments of about 40 kb. Using T4 ligase, these DNA fragments were ligated to Bac vector pBAC108L (Stratagene) or pFOS1 (Stratagene) completely digested with the restriction enzyme Hind III. When the former vector was used, the DNA after completion of the ligation was immediately introduced into *E. coli* by electroporation. When the latter vector was used, the DNA after completion of the ligation was packed into λ phage particles in a test tube using GIGA Pack Gold (Stratagene). Then, the DNA was introduced into *E. coli* by infecting the *E. coli* with these particles. Chloramphenicol-resistant *E. coli* populations obtained by these methods were designated BAC library and Fosmid library. Those clones which are appropriate to cover the chromosomal DNA of JCM 9974 were selected from each of the libraries, and the clones were aligned.

EXAMPLE 4

Determination of the Base Sequence for Each of the BAC or Fosmid Clones

For each of the aligned BAC or Fosmid clones, the base sequence was determined one by one by the following procedures. Briefly, the DNA of each of the BAC or Fosmid clones recovered from *E. coli* was made into fragments by sonication, and fragments of 1 kb and 2 kb were recovered by agarose gel electrophoresis. By inserting these fragments into the Hinc II site of plasmid vector pUC118 (Takara), 500 shotgun clones were prepared for each of the BAC or Fosmid clones.

The base sequence for each shotgun clone was determined with Perkin Elmer, ABI Automatic Base Sequence Reader 373 or 377. The base sequences thus obtained from individual shot gun clones were ligated and edited with the base sequence automatic ligation software "Sequencher" to thereby determine the whole base sequence for each of the BAC or Fosmid clones.

EXAMPLE 5

Identification of the Gene of the Present Invention

The thus determined base sequence for each of the BAC or Fosmid clones was analyzed with a large computer to thereby determine the base sequence for the gene of the invention. The base sequence for the gene of the invention is shown in SEQ ID NO: 2, and the amino acid sequence deduced therefrom is shown in SEQ ID NO: 1.

EXAMPLE 6

Construction of an Expression Plasmid

In order to construct restriction sites (for NdeI and XhoI) in the flanking regions of the structural gene region in the gene of the invention, the following DNA primers were synthesized. Using these primers, the restriction sites were introduced into the flanking regions of the gene by PCR.

Upper Primer: 5'-TTTTGAATTCTTA-CATATGGGCAAGGGGCTTTCA-3'

Lower Primer: 5'-TTTTGGTACCTTTGGATCCTTAAGGGT-TAGCTATCCTTT-3'

After the PCR reaction, the DNA was completely digested with the restriction enzymes NdeI and XhoI (at 37° C. for 2 hours). Then, the structural gene was purified.

Plasmid pET-11a (Stratagene) was digested with the restriction enzymes NdeI and XhoI, and purified. Thereafter, the resultant fragments were reacted with the structural gene obtained above and T4 ligase at 16° C. for 2 hours. A part of the ligated DNA was introduced into competent cells of E. coli-XL1-BlueMRF' to thereby obtain transformant colonies. From these colonies, the expression plasmid was purified by the alkali method.

EXAMPLE 7

Expression of the Recombinant Gene

Using the expression plasmid obtained in Example 6 above, E. coli BL21 (DE3) (Novagen) was transformed. The resultant transformant was cultured in 2YT medium containing ampicillin until the absorbance at 600 nm reached 1. Then, IPTG (isopropyl-b-D-thiogalactopyranoside) was added to the medium, and the cells were cultured for another 6 hours. After the cultivation, the cells were harvested by centrifugation (at 6,000 rpm for 20 minutes).

EXAMPLE 8

Purification of the Thermostable Enzyme

The harvested cells were crushed by adding thereto 2 volumes of alumina. Then, 5 volumes of 10 mM Tris-HCl buffer (pH 8.0) was added thereto to obtain a suspension. The resultant suspension was heated at 85° C. for 30 minutes and centrifuged (at 11,000 rpm for 20 minutes) to thereby obtain a supernatant. The supernatant was adsorbed on a HiTrapQ column (Pharmacia) to obtain active fractions. The resultant solution containing active fractions was concentrated in Centricon (Amicon) and applied to a gel filtration column Superdex200 (Pharmacia) to obtain the enzyme in a purified form.

EXAMPLE 9

Properties of the Enzyme (1) Optimum pH

The determination of the optimum pH for the enzyme activity was conducted as follows. First, 20 mM substrate (acyl-Leu-p-nitroanilide) solutions ranging from 4 to 9 in pH value were prepared with 50 mM sodium acetate buffer, 50 mM phosphate buffer and 50 mM borate buffer. The initial rate of the hydrolysis activity of the enzyme was determined at 85° C. Since the maximum initial rate was obtained at around pH 5.5, the optimum pH was concluded to be 5.5.

(2) Optimum Temperature

The relative activity of the enzyme was examined by adding a specific amount of the enzyme to 20 mM acyl-Leu-p-nitroanilide as a substrate in 50 mM phosphate buffer (pH 7.5) and reacting for 15 minutes. The maximum activity was observed at 90° C. (the optimum temperature) (see FIG. 1).

(3) Thermostability

A solution containing the enzyme (0.1 mg/ml) was heated at 95° C. for 3 hours in 50 mM phosphate buffer (pH 7.5), cooled to 85° C. and examined for residual activity. As a result, no reduction of activity was recognized. Further, circular dichroism (CD) was determined at 25–90° C. As a result, no change was observed in the spectra.

EFFECT OF THE INVENTION

The present invention provides a thermostable acyl peptide hydrolase. With this enzyme, it becomes possible to perform the amino terminal analysis of acylated proteins and peptides at high temperatures. Since the molecule of this enzyme is stable, this enzyme can also be expected to provide an improved resistance to organic solvents.

SEQUENCE LISTING

<160> NUMBER OF SEQ ID NOS: 2

<210> SEQ ID NO 1
<211> LENGTH: 632
<212> TYPE: PRT
<213> ORGANISM: Pyrococcus horikoshii

<400> SEQUENCE: 1

```
Met Gly Lys Gly Leu Ser Glu Lys Asp Leu Gly Lys Phe Lys Leu Val
 1               5                  10                  15

Gly Asn Val Asp Val Phe Lys Gly Lys Ala Val Phe Gln Val Thr Glu
                20                  25                  30

Ile Ser Leu Lys Asp Asp Asp Tyr Phe Ser Lys Leu Tyr Leu Tyr Asp
            35                  40                  45

Gly Lys Arg Val Lys Pro Phe Thr Ser Gly Asn Lys Asp Ser Asn Pro
        50                  55                  60

Arg Phe Ser Pro Asn Gly Lys Leu Ile Ala Phe Thr Ser Lys Arg Asp
    65                  70                  75                  80
```

-continued

```
Lys Glu Gly Lys Glu Ser Glu Leu Tyr Val Ile Pro Thr Asp Gly Gly
                85                  90                  95
Glu Ala Arg Leu Leu Ala Lys Phe Lys Tyr Gly Ile Lys Asn Leu Arg
            100                 105                 110
Phe Thr Glu Asp Gly Lys Ser Ile Ala Val Val Thr Pro Ile Asp Val
            115                 120                 125
Glu Lys Lys Gly Asn Asp Asp Val His Ile Ile Arg Glu Ile Pro Phe
130                 135                 140
Trp Phe Asn Gly Val Gly Trp Ile Tyr Gly Lys Arg Asn Val Val Tyr
145                 150                 155                 160
Leu Val Asp Val Glu Ser Gly Lys Lys Lys Arg Leu Thr Pro Lys Asn
            165                 170                 175
Leu Asn Val Asp Gln Ile Arg Phe His Asn Gly Arg Leu Tyr Phe Thr
            180                 185                 190
Ala Gln Glu Asp Arg Glu Arg Lys Pro Leu Ile Ser Asp Leu Tyr Val
            195                 200                 205
Leu Glu Asn Arg Lys Val Arg Lys Leu Thr Pro Gly Lys Trp Arg Ile
210                 215                 220
Leu Asp Phe Leu Pro Leu Asp Asp Gly Ser Phe Val Leu Lys Ala Asn
225                 230                 235                 240
Thr Leu Glu Arg Gly Ile Pro Thr Asn Ala His Ile Tyr His Tyr Asp
            245                 250                 255
Pro Lys Thr Gly Glu Leu Lys Lys Leu Thr Lys Asp Leu Asp Arg Asn
            260                 265                 270
Ala Tyr Asn Ser Leu Asn Ser Asp Val Arg Gly Ser Gln Arg Ala Glu
            275                 280                 285
Leu Val Tyr Lys Glu Gly Trp Ile Tyr Tyr Val Ala Thr Asp Gly Pro
290                 295                 300
Arg Ala Asn Leu Phe Arg Val Asn Leu Asp Gly Lys Ile Glu Arg Val
305                 310                 315                 320
Ile Gly Gly Asp Arg Ser Val Glu Ser Phe Asp Ile Gly Asp Tyr Ile
            325                 330                 335
Ala Phe Thr Ala Gln Asp Ala Val Thr Pro Thr Glu Leu Tyr Ile Tyr
            340                 345                 350
Arg Asp Gly Lys Glu Lys Lys Val Thr Asp Phe Asn Lys Trp Ile Lys
            355                 360                 365
Gly Tyr Thr Leu Ser Lys Pro Glu His Phe Lys Val Lys Ala Ser Asp
            370                 375                 380
Gly Val Glu Ile Asp Ala Trp Val Met Lys Pro Val Asn Phe Arg Lys
385                 390                 395                 400
Gly Lys Lys Tyr Pro Ala Ile Leu Glu Ile His Gly Gly Pro Lys Thr
            405                 410                 415
Ala Tyr Gly Tyr Ala Phe Met His Glu Phe His Val Leu Thr Ser Lys
            420                 425                 430
Gly Phe Val Val Ile Phe Ser Asn Pro Arg Gly Ser Asp Gly Tyr Gly
            435                 440                 445
Glu Glu Phe Ala Asp Ile Arg Gly His Tyr Gly Glu Arg Asp Tyr Gln
            450                 455                 460
Asp Leu Met Glu Val Val Asp Glu Ala Leu Arg Arg Phe Asp Phe Ile
465                 470                 475                 480
Asp Gly Glu Arg Leu Gly Val Thr Gly Gly Ser Tyr Gly Gly Phe Met
            485                 490                 495
```

```
Thr Asn Trp Ile Val Gly His Thr Asn Arg Phe Lys Ala Ala Val Thr
            500                 505                 510

Gln Arg Ser Ile Ser Asn Trp Ile Ser Phe Phe Gly Thr Thr Asp Ile
            515                 520                 525

Gly Tyr Tyr Phe Ala Pro Asp Gln Ile Gly Lys Asp Pro Trp Ser Asn
            530                 535                 540

Leu Glu Gly Tyr Trp Glu Lys Ser Pro Leu Lys Tyr Ala Pro Asn Val
545                 550                 555                 560

Glu Thr Pro Leu Leu Ile Ile His Ser Thr Glu Asp Tyr Arg Cys Trp
            565                 570                 575

Leu Pro Glu Ala Leu Gln Leu Phe Ile Ser Leu Lys Tyr Leu Gly Lys
            580                 585                 590

Arg Val Glu Leu Ala Ile Phe Pro Gly Glu Asn His Asp Leu Ser Arg
            595                 600                 605

Ser Gly Lys Pro Lys His Arg Val Lys Arg Leu Glu Leu Ile Ala Gly
            610                 615                 620

Trp Met Glu Lys Trp Leu Lys Gly
625                 630

<210> SEQ ID NO 2
<211> LENGTH: 1896
<212> TYPE: DNA
<213> ORGANISM: Pyrococcus horikoshii
<220> FEATURE:
<221> NAME/KEY: CDS
<222> LOCATION: (1)..(1896)

<400> SEQUENCE: 2 atg ggc aag ggg ctt tca gag aaa gat tta ggg aag ttc aag ctt gtg     48
Met Gly Lys Gly Leu Ser Glu Lys Asp Leu Gly Lys Phe Lys Leu Val
1               5                   10                  15 ggt aat gta gat gta ttt aag gga aaa gcg gtc ttt caa gta acg gag     96
Gly Asn Val Asp Val Phe Lys Gly Lys Ala Val Phe Gln Val Thr Glu
            20                  25                  30 ata agc ctc aaa gac gat gat tac ttc tct aag ctt tac ctc tac gat    144
Ile Ser Leu Lys Asp Asp Asp Tyr Phe Ser Lys Leu Tyr Leu Tyr Asp
        35                  40                  45 gga aag agg gta aaa ccc ttc acc tca ggg aac aag gat tct aat cca    192
Gly Lys Arg Val Lys Pro Phe Thr Ser Gly Asn Lys Asp Ser Asn Pro
    50                  55                  60 agg ttc tct cca aat ggg aag ctt ata gca ttt acc tca aag agg gat    240
Arg Phe Ser Pro Asn Gly Lys Leu Ile Ala Phe Thr Ser Lys Arg Asp
65                  70                  75                  80 aag gaa gga aag gaa tca gag ctc tac gtg att cca acg gat ggg gga    288
Lys Glu Gly Lys Glu Ser Glu Leu Tyr Val Ile Pro Thr Asp Gly Gly
                85                  90                  95 gag gcc aga ctt tta gca aag ttc aaa tac ggg ata aag aac ctg cgc    336
Glu Ala Arg Leu Leu Ala Lys Phe Lys Tyr Gly Ile Lys Asn Leu Arg
            100                 105                 110 ttt acc gag gat ggg aaa agt ata gcc gtg gtt acc cct ata gac gtt    384
Phe Thr Glu Asp Gly Lys Ser Ile Ala Val Val Thr Pro Ile Asp Val
        115                 120                 125 gag aaa aaa ggg aat gat gac gtt cac att ata agg gaa ata cca ttc    432
Glu Lys Lys Gly Asn Asp Asp Val His Ile Ile Arg Glu Ile Pro Phe
    130                 135                 140 tgg ttt aat gga gtt ggc tgg atc tac gga aaa aga aac gtt gtc tac    480
Trp Phe Asn Gly Val Gly Trp Ile Tyr Gly Lys Arg Asn Val Val Tyr
145                 150                 155                 160 ctt gtt gac gtt gag agc ggg aag aaa aag aga cta act cca aag aac    528
```

-continued

```
                Leu Val Asp Val Glu Ser Gly Lys Lys Arg Leu Thr Pro Lys Asn
                                165                 170                 175 cta aat gtt gat cag ata agg ttc cac aac ggt aga cta tac ttc acg          576
Leu Asn Val Asp Gln Ile Arg Phe His Asn Gly Arg Leu Tyr Phe Thr
            180                 185                 190 gcc caa gag gat agg gaa agg aaa cct ctg ata tcc gat ctt tac gtc          624
Ala Gln Glu Asp Arg Glu Arg Lys Pro Leu Ile Ser Asp Leu Tyr Val
        195                 200                 205 ctc gag aat aga aaa gtt agg aag ctg acc cca ggg aag tgg agg ata          672
Leu Glu Asn Arg Lys Val Arg Lys Leu Thr Pro Gly Lys Trp Arg Ile
    210                 215                 220 ctc gac ttc ctc ccc ctt gat gac gga agc ttc gta ctt aag gct aac          720
Leu Asp Phe Leu Pro Leu Asp Asp Gly Ser Phe Val Leu Lys Ala Asn
225                 230                 235                 240 act tta gaa agg gga atc cca acc aac gcc cac atc tac cac tac gat          768
Thr Leu Glu Arg Gly Ile Pro Thr Asn Ala His Ile Tyr His Tyr Asp
                245                 250                 255 ccc aag aca gga gaa ctt aag aag ctc aca aag gat tta gac agg aac          816
Pro Lys Thr Gly Glu Leu Lys Lys Leu Thr Lys Asp Leu Asp Arg Asn
            260                 265                 270 gct tac aac tcc tta aac tcc gat gtt cga gga agt cag agg gcc gag          864
Ala Tyr Asn Ser Leu Asn Ser Asp Val Arg Gly Ser Gln Arg Ala Glu
        275                 280                 285 ctt gtg tac aag gag ggg tgg atc tac tat gtc gca acg gat ggc cct          912
Leu Val Tyr Lys Glu Gly Trp Ile Tyr Tyr Val Ala Thr Asp Gly Pro
    290                 295                 300 agg gca aac ctc ttt agg gtc aac tta gat gga aag att gaa agg gta          960
Arg Ala Asn Leu Phe Arg Val Asn Leu Asp Gly Lys Ile Glu Arg Val
305                 310                 315                 320 ata ggt gga gat aga agc gtt gaa agc ttc gat ata ggg gat tac ata         1008
Ile Gly Gly Asp Arg Ser Val Glu Ser Phe Asp Ile Gly Asp Tyr Ile
                325                 330                 335 gct ttc acg gct caa gat gct gta acc cca act gag ctg tac ata tac         1056
Ala Phe Thr Ala Gln Asp Ala Val Thr Pro Thr Glu Leu Tyr Ile Tyr
            340                 345                 350 agg gat gga aag gag aag aag gtt acc gac ttt aac aaa tgg ata aag         1104
Arg Asp Gly Lys Glu Lys Lys Val Thr Asp Phe Asn Lys Trp Ile Lys
        355                 360                 365 ggt tac acc ctt tca aaa cct gaa cac ttt aag gtt aaa gca agt gac         1152
Gly Tyr Thr Leu Ser Lys Pro Glu His Phe Lys Val Lys Ala Ser Asp
    370                 375                 380 ggg gtt gaa ata gat gcc tgg gta atg aaa ccg gtg aac ttc agg aaa         1200
Gly Val Glu Ile Asp Ala Trp Val Met Lys Pro Val Asn Phe Arg Lys
385                 390                 395                 400 gga aag aag tat cca gct att cta gag atc cac ggt ggt cct aaa acc         1248
Gly Lys Lys Tyr Pro Ala Ile Leu Glu Ile His Gly Gly Pro Lys Thr
                405                 410                 415 gct tac ggt tac gct ttt atg cac gag ttc cac gtt tta acc tct aaa         1296
Ala Tyr Gly Tyr Ala Phe Met His Glu Phe His Val Leu Thr Ser Lys
            420                 425                 430 ggc ttc gtc gtg ata ttc tca aat cct aga ggg agc gat ggc tac gga         1344
Gly Phe Val Val Ile Phe Ser Asn Pro Arg Gly Ser Asp Gly Tyr Gly
        435                 440                 445 gag gag ttc gcg gat ata agg gga cac tat ggg gag agg gat tac cag         1392
Glu Glu Phe Ala Asp Ile Arg Gly His Tyr Gly Glu Arg Asp Tyr Gln
    450                 455                 460 gat tta atg gag gta gtc gat gaa gca tta agg aga ttt gac ttc ata         1440
Asp Leu Met Glu Val Val Asp Glu Ala Leu Arg Arg Phe Asp Phe Ile
465                 470                 475                 480
```

-continued

| | |
|---|---|
| gat ggg gaa agg cta gga gtt acc ggg ggt tcc tat ggt ggc ttc atg<br>Asp Gly Glu Arg Leu Gly Val Thr Gly Gly Ser Tyr Gly Gly Phe Met<br>               485                      490               495 | 1488 |
| acg aac tgg ata gtc gga cat acc aac agg ttc aaa gcc gct gta acc<br>Thr Asn Trp Ile Val Gly His Thr Asn Arg Phe Lys Ala Ala Val Thr<br>           500                    505                 510 | 1536 |
| cag aga tca att tca aat tgg ata agc ttc ttc ggg aca acg gat ata<br>Gln Arg Ser Ile Ser Asn Trp Ile Ser Phe Phe Gly Thr Thr Asp Ile<br>       515                  520                   525 | 1584 |
| ggt tat tac ttt gct cca gat caa ata gga aaa gat ccc tgg agc aac<br>Gly Tyr Tyr Phe Ala Pro Asp Gln Ile Gly Lys Asp Pro Trp Ser Asn<br>530                 535                 540 | 1632 |
| ttg gaa ggt tat tgg gaa aag agc cca tta aag tac gct ccc aac gtt<br>Leu Glu Gly Tyr Trp Glu Lys Ser Pro Leu Lys Tyr Ala Pro Asn Val<br>545               550                 555               560 | 1680 |
| gaa act ccc ctg ctt ata atc cac tct acc gaa gac tac agg tgt tgg<br>Glu Thr Pro Leu Leu Ile Ile His Ser Thr Glu Asp Tyr Arg Cys Trp<br>           565                    570               575 | 1728 |
| ctt ccc gag gca ttg caa ctc ttc ata tcc cta aaa tac ctg ggg aag<br>Leu Pro Glu Ala Leu Gln Leu Phe Ile Ser Leu Lys Tyr Leu Gly Lys<br>           580                   585               590 | 1776 |
| aga gtt gaa ttg gca ata ttc cca gga gaa aat cat gac cta agt aga<br>Arg Val Glu Leu Ala Ile Phe Pro Gly Glu Asn His Asp Leu Ser Arg<br>       595                  600                 605 | 1824 |
| tct ggg aag cca aag cac agg gtt aaa aga ctt gaa cta ata gca gga<br>Ser Gly Lys Pro Lys His Arg Val Lys Arg Leu Glu Leu Ile Ala Gly<br>610                 615                 620 | 1872 |
| tgg atg gag aaa tgg ctt aaa gga<br>Trp Met Glu Lys Trp Leu Lys Gly<br>625               630 | 1896 |

What is claimed is:

1. A substantially purified polypeptide characterized as:
   (a) hydrolyzing acyl peptides;
   (b) having an optimum temperature range of 90–95° C.;
   (c) having [anoptimum] an optimum pH range of 5.0–6.0;
   (d) being stable at 95° C. for 3 hours at pH 7.5; and
   (e) having a molecular weight of about 60 kD as determined by SDS-PAGE.

2. The polypeptide of claim 1, wherein the polypeptide has an amino acid sequence as shown in SEQ ID NO:1.

3. The polypeptide of claim 1, wherein the polypeptide has an amino acid sequence as shown in SEQ ID NO:1 having a deletion, substitution, or addition of at least one amino acid.

* * * * *